US 8,626,533 B2

(12) United States Patent
Rao et al.

(10) Patent No.: US 8,626,533 B2
(45) Date of Patent: Jan. 7, 2014

(54) PATIENT DATA MINING WITH POPULATION-BASED ANALYSIS

(75) Inventors: R. Bharat Rao, Berwyn, PA (US); Sathyakama Sandilya, Cranbury, NJ (US)

(73) Assignees: Siemens Medical Soultions USA, Inc., Malvern, PA (US); Siemens Corporation, Iselin, NJ (US)

( * ) Notice: Subject to any disclaimer, the term of this patent is extended or adjusted under 35 U.S.C. 154(b) by 1971 days.

(21) Appl. No.: 10/287,329

(22) Filed: Nov. 4, 2002

(65) Prior Publication Data

US 2003/0125988 A1 Jul. 3, 2003

Related U.S. Application Data

(60) Provisional application No. 60/335,542, filed on Nov. 2, 2001.

(51) Int. Cl.
| | |
|---|---|
| *G06Q 10/00* | (2012.01) |
| *G06Q 50/00* | (2012.01) |
| *A61B 5/00* | (2006.01) |
| *G06F 19/00* | (2011.01) |

(52) U.S. Cl.
USPC .................................................. 705/3; 705/2

(58) Field of Classification Search
USPC ......................................................... 705/3, 2
See application file for complete search history.

(56) References Cited

U.S. PATENT DOCUMENTS

| 4,946,679 A | 8/1990 | Thys-Jacobs |
| 5,172,418 A | 12/1992 | Ito et al. |
| 5,307,262 A | 4/1994 | Ertel |
| 5,359,509 A | 10/1994 | Little et al. |
| 5,365,425 A | 11/1994 | Torma et al. |

(Continued)

FOREIGN PATENT DOCUMENTS

| DE | 198 20 276 | 11/1999 |
| EP | 0 596 247 A2 | 5/1994 |

(Continued)

OTHER PUBLICATIONS

"Machine Learning and Data Mining", Mitchell, Communications of the ACM, Nov. 1999, ACM, USA, Online!, vol. 42, No. 11, Nov. 1999, pp. 30-36, retrieved from internet: http://portal.acm.org/ft_gateway.cfm?

(Continued)

*Primary Examiner* — Luke Gilligan
*Assistant Examiner* — Kristine Rapillo
(74) *Attorney, Agent, or Firm* — Joshua B Ryan

(57) ABSTRACT

A system and method for analyzing population-based patient information is provided. The method includes the steps of data mining a plurality of patient records using a domain knowledge base relating to a disease of interest; compiling the mined data into a plurality of structured patient records; inputting at least one patient criteria relating to the disease of interest; and extracting at least one structured patient record matching the at least one patient criteria. The system includes a data miner for mining information from the plurality of patient records using a domain knowledge base relating to a disease of interest and for compiling the mined data into a plurality of structured patient records; an interface for inputting at least one patient criteria relating to the disease of interest; and a processor adapted for extracting at least one of the structured patient records matching the at least one patient criteria.

17 Claims, 5 Drawing Sheets

(56) References Cited

U.S. PATENT DOCUMENTS

| | | | |
|---|---|---|---|
| 5,508,912 A | 4/1996 | Schneiderman | |
| 5,544,044 A | 8/1996 | Leatherman | |
| 5,557,514 A | 9/1996 | Seare et al. | |
| 5,652,842 A | 7/1997 | Siegrist, Jr. et al. | |
| 5,657,255 A | 8/1997 | Fink et al. | |
| 5,664,109 A * | 9/1997 | Johnson et al. | 705/2 |
| 5,669,877 A | 9/1997 | Blomquist | |
| 5,706,441 A | 1/1998 | Lockwood | |
| 5,724,379 A | 3/1998 | Perkins et al. | |
| 5,724,573 A | 3/1998 | Agrawal et al. | |
| 5,738,102 A | 4/1998 | Lemelson | |
| 5,811,437 A | 9/1998 | Singh et al. | |
| 5,832,450 A | 11/1998 | Myers et al. | |
| 5,835,897 A | 11/1998 | Dang | |
| 5,899,998 A | 5/1999 | McGauley et al. | |
| 5,903,889 A | 5/1999 | de la Huerga et al. | |
| 5,908,383 A | 6/1999 | Brynjestad | |
| 5,924,073 A | 7/1999 | Tyuluman et al. | |
| 5,924,074 A | 7/1999 | Evans | |
| 5,939,528 A | 8/1999 | Clardy et al. | |
| 5,991,731 A | 11/1999 | Colon et al. | |
| 6,039,688 A | 3/2000 | Douglas et al. | |
| 6,067,466 A | 5/2000 | Selker et al. | |
| 6,076,088 A | 6/2000 | Paik et al. | |
| 6,078,894 A | 6/2000 | Clawson et al. | |
| 6,081,786 A | 6/2000 | Barry et al. | |
| 6,083,693 A | 7/2000 | Nandabalan et al. | |
| 6,108,635 A | 8/2000 | Herren et al. | |
| 6,125,194 A | 9/2000 | Yeh et al. | |
| 6,128,620 A | 10/2000 | Pissanos et al. | |
| 6,139,494 A | 10/2000 | Cairnes | |
| 6,151,581 A | 11/2000 | Kraftson et al. | |
| 6,173,280 B1 | 1/2001 | Ramkumar et al. | |
| 6,196,970 B1 | 3/2001 | Brown | |
| 6,212,519 B1 | 4/2001 | Segal | |
| 6,212,526 B1 | 4/2001 | Chaudhuri et al. | |
| 6,253,186 B1 | 6/2001 | Pendleton, Jr. | |
| 6,259,890 B1 | 7/2001 | Driscoll et al. | |
| 6,266,645 B1 | 7/2001 | Simpson | |
| 6,272,472 B1 * | 8/2001 | Danneels et al. | 705/27 |
| 6,322,502 B1 | 11/2001 | Schoenberg et al. | |
| 6,322,504 B1 | 11/2001 | Kirshner | |
| 6,338,042 B1 | 1/2002 | Paizis | |
| 6,381,576 B1 | 4/2002 | Gilbert | |
| 6,478,737 B2 | 11/2002 | Bardy | |
| 6,484,144 B2 | 11/2002 | Martin et al. | |
| 6,523,019 B1 | 2/2003 | Borthwick | |
| 6,529,876 B1 | 3/2003 | Dart | |
| 6,551,243 B2 * | 4/2003 | Bocionek et al. | 600/300 |
| 6,551,266 B1 | 4/2003 | Davis, Jr. | |
| 6,587,829 B1 | 7/2003 | Camarda et al. | |
| 6,611,825 B1 | 8/2003 | Billheimer et al. | |
| 6,611,846 B1 * | 8/2003 | Stoodley | 707/104.1 |
| 6,641,532 B2 | 11/2003 | Iliff | |
| 6,645,959 B1 | 11/2003 | Bakker-Arkema et al. | |
| 6,754,655 B1 | 6/2004 | Segal | |
| 6,802,810 B2 | 10/2004 | Ciarniello et al. | |
| 6,804,656 B1 | 10/2004 | Rosenfeld et al. | |
| 6,826,536 B1 | 11/2004 | Forman | |
| 6,839,678 B1 | 1/2005 | Schmidt et al. | |
| 6,903,194 B1 | 6/2005 | Sato et al. | |
| 6,915,254 B1 | 7/2005 | Heinze et al. | |
| 6,915,266 B1 | 7/2005 | Saeed et al. | |
| 6,961,687 B1 | 11/2005 | Myers, Jr. et al. | |
| 6,988,075 B1 | 1/2006 | Hacker | |
| 7,058,658 B2 | 6/2006 | Mentzer | |
| 7,130,457 B2 | 10/2006 | Kaufman et al. | |
| 7,249,006 B2 | 7/2007 | Lombardo et al. | |
| 7,307,543 B2 | 12/2007 | Rosenfeld et al. | |
| 7,353,238 B1 | 4/2008 | Gliklich | |
| 7,630,908 B1 | 12/2009 | Amrien et al. | |
| 2001/0011243 A1 | 8/2001 | Dembo et al. | |
| 2001/0023419 A1 | 9/2001 | LaPointe et al. | |
| 2001/0032195 A1 | 10/2001 | Graichen et al. | |
| 2001/0051882 A1 | 12/2001 | Murphy et al. | |
| 2002/0002474 A1 | 1/2002 | Michelson et al. | |
| 2002/0010597 A1 | 1/2002 | Mayer et al. | |
| 2002/0026332 A1 | 2/2002 | Snowden et al. | |
| 2002/0032581 A1 | 3/2002 | Reitberg | |
| 2002/0035316 A1 | 3/2002 | Drazen | |
| 2002/0077853 A1 | 6/2002 | Boru et al. | |
| 2002/0082480 A1 | 6/2002 | Riff et al. | |
| 2002/0087361 A1 | 7/2002 | Benigno et al. | |
| 2002/0099570 A1 * | 7/2002 | Knight | 705/2 |
| 2002/0123905 A1 | 9/2002 | Goodroe et al. | |
| 2002/0138492 A1 | 9/2002 | Kil | |
| 2002/0138524 A1 | 9/2002 | Ingle et al. | |
| 2002/0143577 A1 | 10/2002 | Shiffman et al. | |
| 2002/0165736 A1 | 11/2002 | Tolle et al. | |
| 2002/0173990 A1 | 11/2002 | Marasco | |
| 2002/0177759 A1 | 11/2002 | Schoenberg et al. | |
| 2003/0028401 A1 | 2/2003 | Kaufman et al. | |
| 2003/0046114 A1 * | 3/2003 | Davies et al. | 705/3 |
| 2003/0050794 A1 | 3/2003 | Keck | |
| 2003/0108938 A1 | 6/2003 | Pickar et al. | |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0120514 A1 | 6/2003 | Rao et al. | |
| 2003/0125984 A1 | 7/2003 | Rao et al. | |
| 2003/0125985 A1 | 7/2003 | Rao et al. | |
| 2003/0126101 A1 | 7/2003 | Rao et al. | |
| 2003/0130871 A1 | 7/2003 | Rao et al. | |
| 2003/0135391 A1 | 7/2003 | Edmundson et al. | |
| 2003/0208382 A1 | 11/2003 | Westfall | |
| 2004/0078216 A1 | 4/2004 | Toto | |
| 2004/0184644 A1 | 9/2004 | Leichter et al. | |
| 2004/0243586 A1 | 12/2004 | Byers | |
| 2005/0187794 A1 | 8/2005 | Kimak | |
| 2005/0191716 A1 | 9/2005 | Surwit et al. | |
| 2006/0064415 A1 | 3/2006 | Guyon et al. | |
| 2006/0136259 A1 | 6/2006 | Weiner et al. | |

FOREIGN PATENT DOCUMENTS

| | | |
|---|---|---|
| EP | 0 641 863 | 3/1995 |
| EP | 0 917 078 A1 | 10/1997 |
| GB | 2 332 544 A | 6/1999 |
| JP | 11328073 A | 11/1999 |
| JP | 2001297157 A | 10/2001 |
| WO | WO 98/29790 | 7/1998 |
| WO | 98/39720 | 9/1998 |
| WO | WO 00/51054 | 8/2000 |
| WO | WO 00/69331 | 11/2000 |
| WO | WO 01/66007 | 9/2001 |
| WO | WO 01/78005 A2 | 10/2001 |
| WO | 01/82173 A1 | 11/2001 |

OTHER PUBLICATIONS

"Data Mining for the Enterprise", Kleissner, System Sciences, 1998, Proceedings of the Thirty-First Hawaii International Conference on Kohala Coast, HI, USA Jan. 6-9, 1998, Los Alamitos, CA, USA, IEEE Comput. Soc. US, Jan. 6, 1998, pp. 295-304.

"Improved Diagnostic and Prognostic Assessments Using Health Management Information Fusion", Roemer et al., 20001 IEEE Autotestcon Proceedings, IEEE Systems Readiness Technology Conference, Autotestcon 2001, vol. CONF. 37, Aug. 20, 2001, pp. 365-377.

"Information Understanding Integrating Data Fusion and Data Mining Processes", Waltz et al, Circuits and Systems, 1998, ISCAS 98, Proceedings of the 1998 IEEE International Symposium on Monterey, CA, USA May 31-Jun. 3, 1998, NY, NY, USA, IEEE, May 31, 1998, pp. 553-556.

"Using Data Mining to Characterize DNA Mutations by Patient Clinical Features", Evans et al., 1997 AMIA Annual Fall Symposium, Proceedings of 1997 AMIA Annual Fall Symposium the Emergence of Internetable Health Care Systems That Really Work, Nashville. TN, pp. 253-257.

"The Colorectal Cancer Recurrence Support (CARES) System", Ong et al., Artificial Intelligence in Medicine, Nov. 1997, Elsevier, Netherlands, vol. 11, No. 3, pp. 175-188.

(56) References Cited

OTHER PUBLICATIONS

"Database System Support for Multidimensional Data Analysis in Environmental Epidemiology", Kamp et al., Database Engineering and Applications Symposium, 1997, Ideas 97, Proceedings, International Montreal, Que, Canada, Aug. 25-27, 1997, Los Alamitos, CA, USA, IEEE Comput. Soc., US, pp. 180-188.
Rao et al., "Data Mining for Disease Management: Adding Value to Patient Records". Electromedia, Online, vol. 68, 2000, pp. 63-67.
King et al., "MEDUS/A: Distributing Database Management for Medical Research", Proceedings of Computer Networks Compcon 82, Sep. 20-23, 1982, pp. 635-642.
Boxwala et al., "Architecture for a Multipurpose Guideline Execution Engine", Proc. AMIA Symp 1999, pp. 701-705.
Guidance for Institutional Review Boards and Clinical Investigators 1998 Update. Sep. 1998, U.S. Food and Drug Administration.
Kassirer, "The Use and Abuse of Practice Profiles", Mar. 3, 1994, The New England Journal of Medicine, vol. 330:634-636.
Chen "Do "America's Best Hospitals" Perform Better for Acute Myocardial Infarctions?", Jan. 28, 1999, The New England Journal of Medicine, vol. 340, No. 4:286-292.
Hofer, "The Unreliability of Individual Physician "Report Cards" for Assessing the Costs and Quality of Care of a Chronic Disease", Jun. 9, 1999, JAMA, vol. 281, No. 22:2098-2105.
Grimes, "Structure, Models and Meaning, Is "Unstructured" Data Merely Unmodeled?", Mar. 1, 2005, Intelligent Enterprise, http://www.intelligententerprise.com/show/Article.jhtml?articleID=59301538.
Berkus, "Unstructured Data as an Oxymoron", Sep. 1, 2005, ITtoolbox Blogs, http://blogs.ittoolbox.com/database/soup/archives/unstructured-data-as-an-oxymoron-5588.
Larsen, "Fast and effective text mining using linear-time document clustering", 1999, ACM Press, Conference on Knowledge Discovery in Data, Proceedings of the fifth ACM SIGKDD International Conference on Knowledge Discovery and Data Mining, pp. 16-22.
Rao, "From Unstructured Data to Actionable Intelligence", IT Pro, Nov./Dec. 2003, pp. 29-35.
Dato, et al., The Nation's Current Capacity for the Early Detection of Public Health Threats Including Bioterrorism, Agency for Healthcare Research and Quality, Jun. 8, 2001.
Hanson, et al., Bayesian Classification Theory, Technical Report FIA-90-12-7-01, 1991, pp. 1-10.
Diadoo, Cindy A., An Assessment for the Need of a Bioterrorism Preparedness Plan at Hospital XYZ in Minnesota, The Graduate College, University of Wisconsin-Stout, Dec. 1999, pp. 1-57.
Wagner, et al., Availability and Comparative Value of Data Elements Required for an Effective Bioterrorism Detection System, Nov. 28, 2001, Agency for Healthcare Research and Quality, pp. 1-184.
Bregg, et al., Assessment of Diagnostic Tests When Disease is Subject to Selection Bias, Biometrics, vol. 39, No. 1, Mar. 1983, pp. 207-215.
Un Yong Nahm et al.: A Mutually Beneficial Integration of Data Mining and Information Extraction Proceedings AAAI, National Conference on Artificial Intelligence Jul. 30, 2000, pp. 627, 632, XP008002223 International Search Report.
Mills, "Computer Technology of the Not-too-distant Future", Sep. 1993, Medical Laboratory Observer, vol. 25, No. 9, p. 78.
Duda, "Pattern Classification", 2001, John Wiley & Sons, Inc., p. vii-xx, Chapter 1.
Hudson, "The feasibility of using automated data to assess guideline-concordant care for schizophrenia", Dec. 4, 1999, Journal of Medical Systems, vol. 23, No. 4, pp. 299-307.
PR Newsire, Diabetes Health Management Award Honors Mayor Clinic's Zimmerman, Sep. 25, 2000.
Hudson, "CAATS and compliance", Apr. 1998, The Internal Auditor, vol. 55, No. 2, p. 25.

\* cited by examiner

PATIENT DATA MINING WITH POPULATION-BASED ANALYSIS

CROSS REFERENCE TO RELATED APPLICATIONS

This application claims the benefit of U.S. Provisional Application Ser. No. 60/335,542, filed on Nov. 2, 2001, which is incorporated by reference herein in its entirety.

FIELD OF THE INVENTION

The present invention relates to medical information processing systems, and, more particularly to a computerized system and method for performing outcome analysis on a patient based on population-based information derived from various sources and for conducting retrospective studies on the population-based information.

BACKGROUND OF THE INVENTION

The proper care of medical patients is essential for optimal treatment of their medical conditions. Typically, a patient having a particular condition/ailment is prescribed a medicine or treatment based upon established treatment guidelines. The treatment guidelines outline, inter alia, the specific dosages of medicines, the frequency in which dosages should be administered, instructions on how dosages should be administered and the time-lines for therapeutic treatments. Oftentimes, treatment for new patients is administered directly from the treatment guidelines with little variation. These guidelines are typically derived through prospective medical studies. Prospective medical studies, namely, randomized clinical trials, are studies wherein researchers empirically test hypotheses in near ideal conditions by screening the patient population, ensuring that patient care diligently follows the guidelines and recording all relevant data. Such practices fail to take full advantages of historical medical data, rather, relying only on success rates for the patients that rigidly adhered to the treatment guidelines. Additionally, clinical trials are very expensive to conduct.

Historical medical data represents a valuable source in the analysis of the patient care process and medical outcomes. As indicated, treatment guidelines have been generated based solely upon the results of treatment on patients who rigidly adhered to the treatment guidelines. However, the number of variables from patient and professional medical care having an impact on the results of patient care is exceedingly high. Moreover, the relationship between these variables is virtually unknown. Accordingly, the ability to fully learn from past medical data could greatly improve patient health care.

Retrospective studies, for example, the analysis of historical medical patient records from a hospital, are complementary to prospective clinical trials. Health-care organizations are accumulating vast stores of patient data, which are a vital tool for knowledge management. Analyzing this already-collected information may lead to insights that can be subsequently verified in a prospective trial. Most importantly, retrospective studies can measure, in a least two ways, the impact of guidelines in real-life clinical settings. First, retrospective studies can determine the effectiveness of the treatment for a patient population that was excluded from clinical trials. For example, patients above 65, or those with other diseases may be excluded in a clinical trial—however, the guideline validated in that trial is now used to treat all hospital patients. Second, patient treatment in a hospital may differ from that in a trial. For instance, the colon cancer guideline mandates commencing chemotherapy within 6 weeks of surgery, which is rigorously enforced in the clinical trial. However, in a hospital, some patients may begin chemotherapy up to 10 weeks after surgery (e.g., they may be too sick or miss appointments). The impact of this delay on a patient's outcome can only be determined via retrospective analysis since it is not ethical to conduct a clinical trial that would test the impact of this delay—in effect, withholding the accepted standard of care.

However, analyzing hospital data is hard for many reasons. First, medical data is very complex to analyze because of its rich structure. Many traditional statistical methods are ill-suited to data with structure, time-sequenced events (medical data has important temporal components) and/or no structure such as free text, images, etc. Second, because the hospital patient data was collected to treat the patient (as opposed to collected for analysis in a clinical trial), it is imperfect in many ways, for example, missing/incorrect/inconsistent data; key outcomes/variables not recorded; bias in data collection, e.g., sick patients get more tests than well ones, (this is perfectly natural from the medical point of view, but has inherent assumptions that may cause problems for many algorithms); and variables collected/treatments change over time, which particularly impacts some long-term diseases whose treatment can span decades. Lastly, there is wide variation in practice among medical professionals determining if a patient is on a guideline and treated properly is difficult to tell.

In view of the above, there exists a need for techniques to collect population-based patient information from a variety of sources, to perform outcome analysis on the collected information, and to conduct retrospective analysis on a large quantity of medical information derived from various sources in a rapid manner.

SUMMARY OF THE INVENTION

A system and method for analyzing population-based patient information is provided.

According to one aspect of the present invention, a method for analyzing patient records is provided including the steps of data mining a plurality of patient records using a domain knowledge base relating to a disease of interest; compiling the mined data into a plurality of structured patient records; inputting at least one patient criteria relating to the disease of interest; and extracting at least one structured patient record matching at least one patient criteria.

According to another aspect of the present invention, a system for analyzing a plurality of patient records includes a data miner for mining information from the plurality of patient records using a domain knowledge base relating to a disease of interest and for compiling the mined data into a plurality of structured patient records; an interface for inputting at least one patient criteria relating to the disease of interest; and a processor adapted for extracting at least one of the structured patient records matching at least one patient criteria.

In a further aspect of the present invention, a method for conducting a retrospective study on a plurality of patient records is provided. The method includes the steps of data mining the plurality of patient records using a domain knowledge base relating to a disease of interest; compiling the mined data into a plurality of structured patient records; inputting a plurality of patient criteria forming a hypothesis relating to the disease of interest; and extracting a plurality of structured patient records matching the plurality of patient criteria. The method further includes the steps of determining patient outcomes from the plurality of structured patient records and validating the hypothesis by comparing the patient outcomes to a suggested outcome.

In another aspect of the present invention, a program storage device readable by a machine, tangibly embodying a program of instructions executable by the machine to perform method steps for analyzing patient records is provided including the method steps of data mining a plurality of patient records using a domain knowledge base relating to a disease of interest; compiling the mined data into a plurality of structured patient records; inputting at least one patient criteria relating to the disease of interest; and extracting at least one structured patient record matching the at least one patient criteria.

BRIEF DESCRIPTION OF THE DRAWINGS

The above and other aspects, features and advantages of the present invention will become more apparent from the following detailed description when taken in conjunction with the accompanying drawings in which.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

A system and method for analyzing population-based medical data is provided. According to an embodiment of the present invention, a computer-based system will compile population-based patient data from various sources, e.g., structured and unstructured, into a structured database for analysis. First, the system will assimilate information from both structured, e.g., financial, and unstructured, e.g., imaging, sources within a computerized patient record (CPR). These data can be automatically extracted, combined, and analyzed in a meaningful way.

The present invention allows for analysis of a large amount of information in a rapid manner, as opposed to the traditional method of medical personnel reviewing each record and transposing their findings. Since information is collected from a variety of sources containing different information relating to specific patients, various criteria or variables can be analyzed to determine their effect on a proposed treatment or guideline.

It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
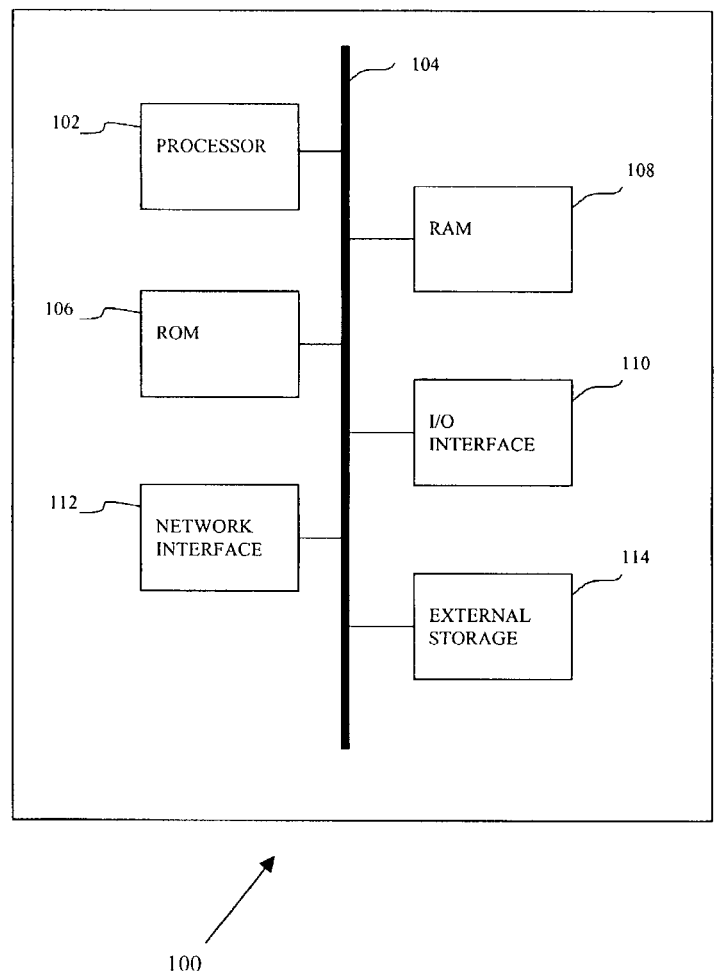
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
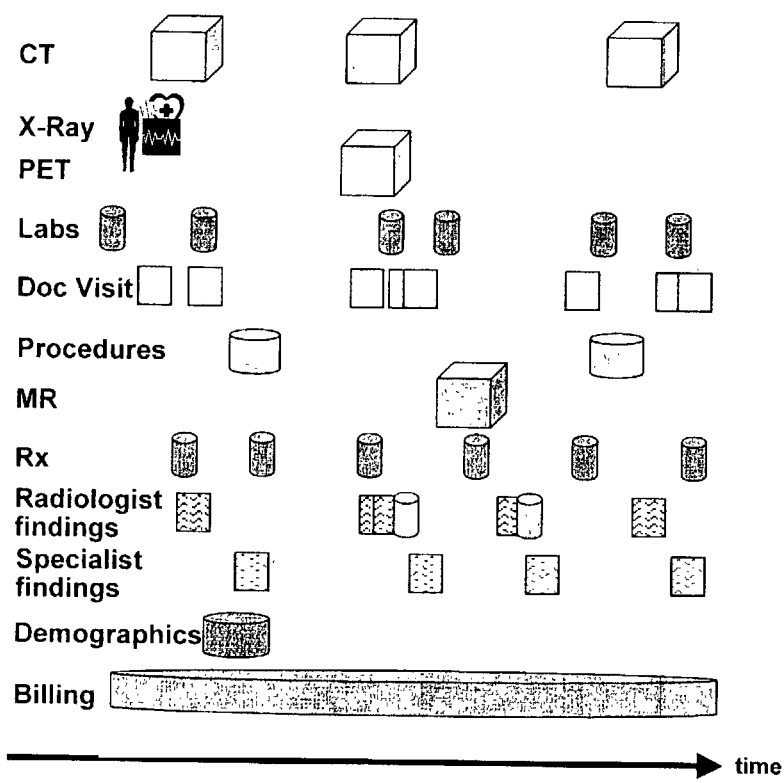
FIG. 2 illustrates an exemplary computerized patient record (CPR)

Increasingly, health care providers are employing automated techniques for information storage and retrieval. The use of a computerized patient record (CPR) to maintain patient information is one such example. As shown in FIG. 2, an exemplary CPR (200) includes information that is collected over the course of a patient's treatment. This information may include, for example, computed tomography (CT) images, X-ray images, laboratory test results, doctor progress notes, details about medical procedures, prescription drug information, radiological reports, other specialist reports, demographic information, and billing (financial) information.

A CPR typically draws from a plurality of data sources, each of which typically reflects a different aspect of a patient's care. Structured data sources, such as financial, laboratory, and pharmacy databases, generally maintain patient information in database tables. Information may also be stored in unstructured data sources, such as, for example, free text, images, and waveforms. Often, key clinical findings are only stored within physician reports, e.g., dictations.

Figure 3:
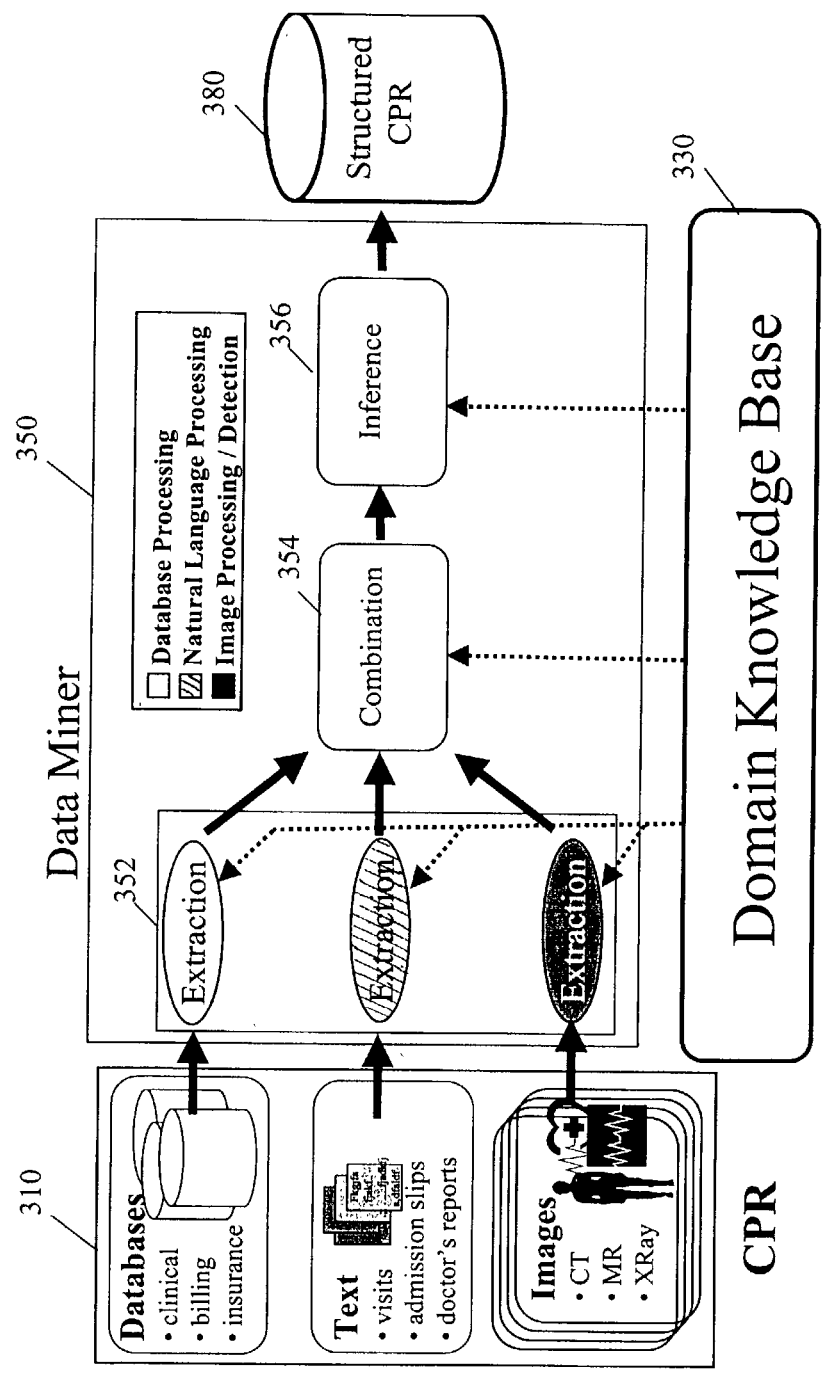
FIG. 3 illustrates an exemplary data mining framework for mining high-quality structured medical information.

FIG. 3 illustrates an exemplary data mining system for mining high-quality structured clinical information using data mining techniques described in "Patient Data Mining," by Rao et al., copending U.S. Published Patent Application No. 2003/0126101 filed herewith, which is incorporated by reference in its entirety. The data mining system includes a data miner (350) that mines information from a CPR (310) using domain-specific knowledge contained in a knowledge base (330). The data miner (350) includes components for extracting information from the CPR (352), combining all available evidence in a principled fashion over time (354), and drawing inferences from this combination process (356). The mined information may be stored in a structured CPR database (380). In this manner, all information contained in a CPR, whether from a structured or unstructured source, will stored in a structured fashion.

The extraction component (352) deals with gleaning small pieces of information from each data source regarding a patient, which are represented as probabilistic assertions about the patient at a particular time. These probabilistic assertions are called elements. The combination component (354) combines all the elements that refer to the same variable at the same time period to form one unified probabilistic assertion regarding that variable. These unified probabilistic assertions are called factoids. The inference component (356) deals with the combination of these factoids, at the same point in time and/or at different points in time, to produce a coherent and concise picture of the progression of the patient's state over time. This progression of the patient's state is called a state sequence.

The present invention can build an individual model of the state of a patient. The patient state is simply a collection of variables or criteria that one may care about relating to the patient. The information of interest may include a state sequence, i.e., the value of the patient state at different points in time during the patient's treatment.

Each of the above components uses detailed knowledge regarding the domain of interest, such as, for example, a disease of interest. This domain knowledge base (330) can come in two forms. It can be encoded as an input to the system, or as programs that produce information that can be understood by the system. The part of the domain knowledge base (330) that is input to the present form of the system may also be learned from data.

Extraction from a text source may be carried out by phrase spotting, which requires a list of rules that specify the phrases of interest and the inferences that can be drawn therefrom. For example, if there is a statement in a doctor's note with the words "There is evidence of metastatic cancer in the liver," then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The data sources include structured and unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Combination includes the process of producing a unified view of each variable at a given point in time from potentially conflicting assertions from the same/different sources. In various embodiments of the present invention, this is performed using domain knowledge regarding the statistics of the variables represented by the elements ("prior probabilities").

Inference is the process of taking all the factoids that are available about a patient and producing a composite view of the patient's progress through disease states, treatment protocols, laboratory tests, etc. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, etc.). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer<cancer=True (probability=0.35), cancer=False (probability=0.65)> (e.g., 35% of patients have cancer). Then, we could combine this assertion with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer=True (probability=0.1), cancer=unknown (probability=0.9)> and
4. <cancer=False (probability=0.4), cancer=unknown (probability=0.6)>.

In this case, we might combine these elements with the base probability of cancer <cancer=True (probability=0.35), cancer=False (probability=0.65)> to conclude, for example, that <cancer=True (prob=0.67), cancer=False (prob=0.33)>.

As mentioned, the extraction component (352) takes information from the CPR (310) to produce probabilistic assertions (elements) about the patient that are relevant to an instant in time or time period. This process is carried out with the guidance of the domain knowledge that is contained in the domain knowledge base (330). The domain knowledge required for extraction is generally specific to each source.

Figure 4:
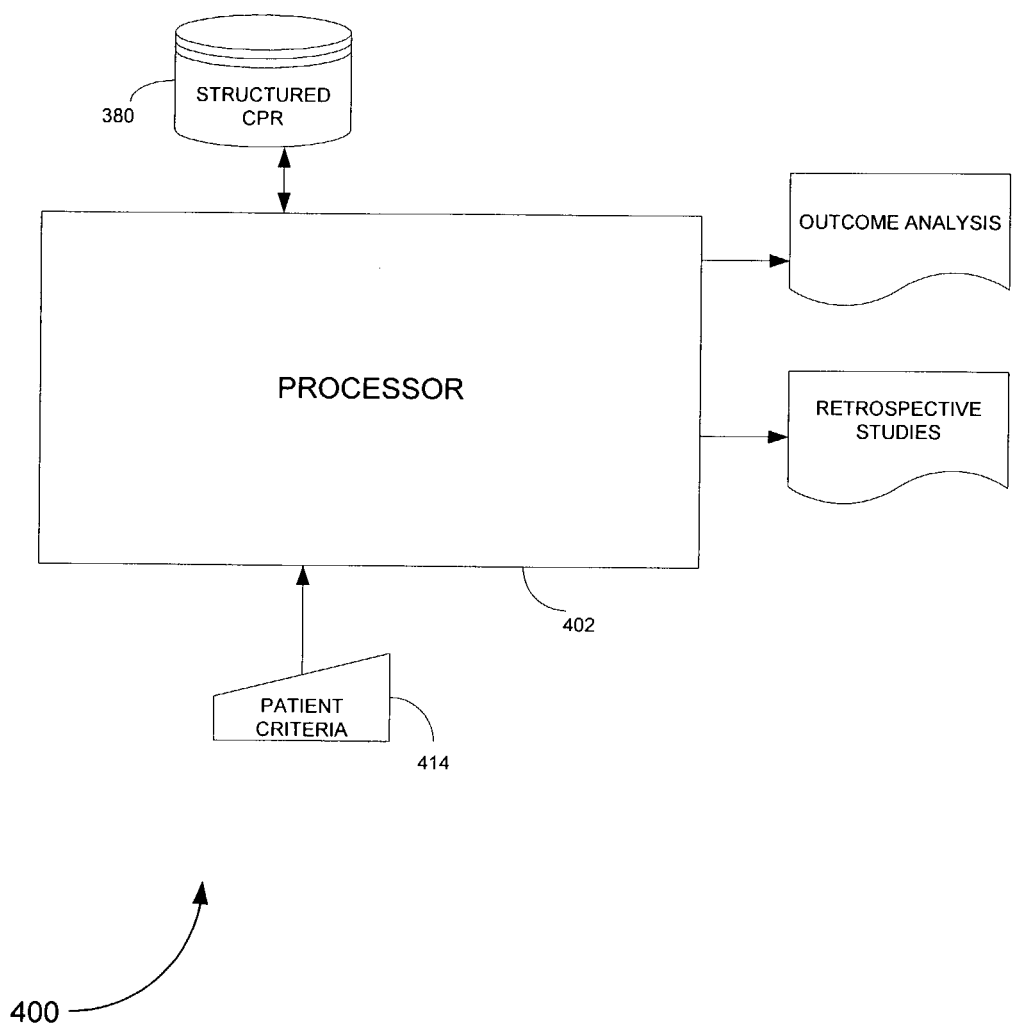
FIG. 4 illustrates a block diagram of an exemplary analysis system according to an embodiment of the present invention.

Referring to FIG. 4, an exemplary analysis system 400 according to an embodiment of the present invention is illustrated. The analysis system 400 includes a processor 402 for extracting information from the structured database 380 and for performing different tasks on the extracted information. Additionally, the processor 402 is adapted to receive manually inputted patient criteria or variables 414 via an I/O interface which will be used to extract specific information from the database 380. Each task performed by the analysis system 200 is performed by an executable module residing either in the processor of the system 402 and/or in a memory device (e.g., RAM, ROM, external storage, etc.) of the system.

Figure 5:
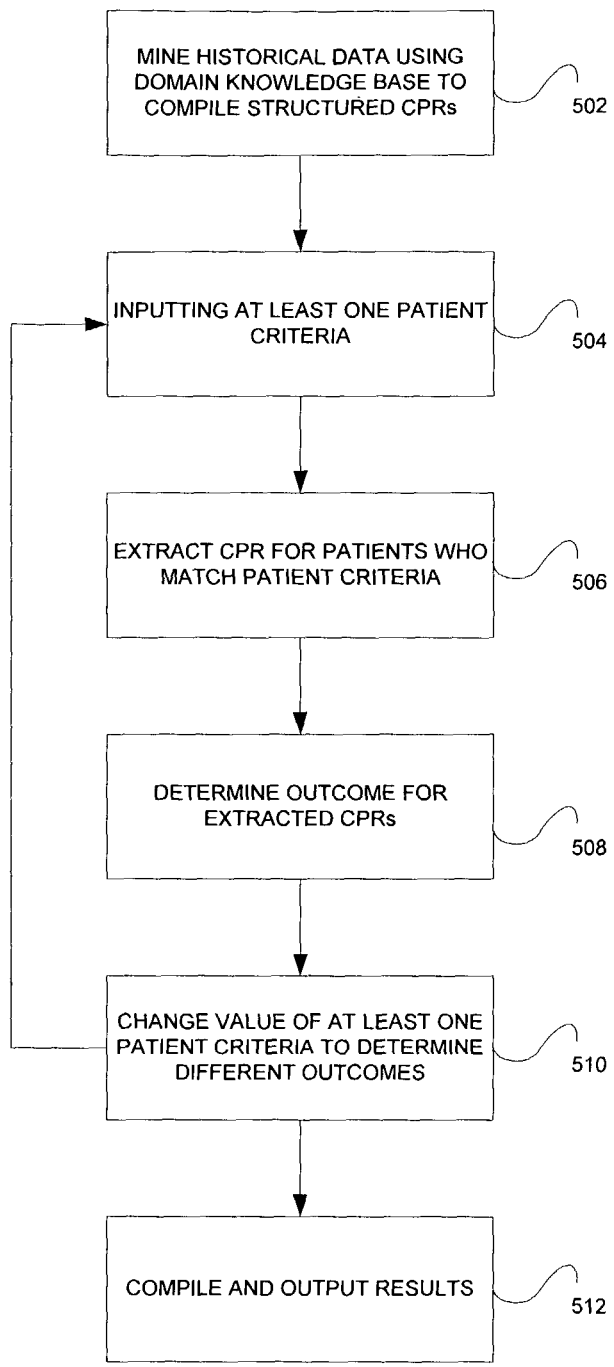
FIG. 5 illustrates a flow diagram for analyzing large amounts of medical information according to an embodiment of the present invention.

Referring to FIG. 5, a flow chart illustrating a method of analyzing population-based data is provided. For example, the problem of unsatisfactory outcomes (e.g., clinical, financial, and length of stay) in patients with diabetes who sustain a myocardial infarction can be examined for a particular hospital.

First, a plurality of computerized patient records is assembled during the course of treatment of a large number of patients over time, for example, in a particular hospital. This historical data is mined using a domain knowledge base relating to a disease of interest and compiled in a structured CPR database (step 502). For example, information is extracted from a variety of sources to identify patients with a confirmed diagnosis of acute myocardial infarction (AMI). This will not be based on ICD-9 codes (which have about 90% accuracy), but on a combination of clinical, laboratory, and EKG findings that meet the MONICA criteria, the internationally accepted standard for identifying AMI patients.

One or more criteria or variables relating to the disease of interest is inputted into the system (step 504). The system extracts patient records from the structured database which conform to the criteria (step 506). For example, once the AMI patients are identified, the system will separate out a subset of patients with diabetes mellitus (e.g., the criteria), based on pharmacy data showing the need for administration of insulin or other anti-diabetic agents, and on lab data showing high blood sugars.

Then, the system determines patient outcomes for the extracted patient records (step 508) and outputs the results. At least one value of the patient criteria may be changed to determine how the change in value of the criteria effects the outcome (step 510). Finally, the system will compile and output the outcome results so the appropriate personnel can review (step 512). The system identifies differences in clinical outcomes, e.g. death, procedures (coronary bypass or angioplasty), infections, etc, and places these results in the context of the accompanying financial, case-mix, treatment, therapy and length of stay-data. The output may be a chart, table, curve, etc. illustrating the effects of the changes in criteria against patient outcomes.

In another embodiment, the system and method of the present invention will perform outcome analysis on a particular patient, for example, a physician may want to determine the best prescription drug for lowering a patient's cholesterol level. The system will extract patient records for patient with a cholesterol level over a predetermined limit, e.g., 250. The physician will enter criteria or variables 414 related to a current state of the patient, e.g., age, blood pressure, LDL cholesterol, HDL cholesterol, etc. The processor 402 will then interact with the structured CPR database 380 to extract patient records that match the criteria of the current patient and will output the patient outcomes versus drug treatments of the extracted records. The physician may change a value of one or more of the criteria or variables, e.g., use of a different drug, changes to the patient's smoking habits, etc., to determine how the outcome is affected by the change, wherein the system will extract new patient records to reflect patient outcomes based on the new set of variables. Since the system can extract different patient records based on different criteria from a large volume of records, the system can perform outcome analysis much faster than in the traditional manner of trying to search by hand patient records with similar information.

Additionally, the system may be used to generate a hypothesis for a potential prospective clinical trial by correlating the inputted criteria to the determined outcomes.

In another embodiment, the system and method of the present invention may be employed to conduct a retrospective study. During a prospective clinical trial, a particular group of people, for example, males ages 25 to 40, may have been observed to determine the most appropriate guideline for treating a particular disease. The guideline developed from the clinical trial is later then applied to all age groups without further testing. The system and method of the present invention will allow a study to be conducted on people excluded from the trial by extracting patient records which match the guideline created during the actual trial but will be restricted by an inputted patient criteria, e.g., females ages 40-50. The system and method of the present invention allow a retrospective study be conducted on a large population of people without the need for someone to manually review a large number of records.

Furthermore, a retrospective study may be conducted to validate the hypothesis generated by correlating the inputted criteria to the determined patient outcomes and, then, comparing the determined patient outcomes to a suggested patient outcome of the hypothesis.

The analysis system and method of the present invention provides for a collection of a large volume of data from various sources, i.e., structured and unstructured, to be analyzed in an efficient and rapid manner. The method and system will provide improve quality of care by allowing medical professionals to perform patient outcome analysis on population-based patient information, e.g., a large quantity of patients treated by a hospital, to determine the most appropriate treatment. Additionally, the system and method of the present invention will reduce costs to researchers and hospitals by allowing retrospective studies to be performed automatically by mining data from varied sources, as opposed to conventional individual review and analysis.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for analyzing patient records, the method comprising:
    data mining, by a processor, a plurality of first patient records including unstructured data, the data mining using a domain knowledge base relating to a disease of interest and mining the unstructured data, the data mining comprising:
    mining from a plurality of different data sources for each of the first patient records, each of the first patient records being for a respective patient;
    for each of a plurality of variables for each patient, extracting different values from multiple of the different data sources such that multiple of the values are provided for each of the variables representing the patient at a same time;
    for each of the plurality of variables for each patient, assigning a probabilistic assertion to each of the values from the different data sources such that the multiple values for each variable are each assigned probability, resulting in different values and respective probabilistic assertions for each variable of the plurality of variables representing each patient; and
    for each of the plurality of variables for each patient, combining by inference the probabilities for each of the values from the different data sources into a unified probability for the respective variable, the unified probability providing a factoid representing a final value for the respective variable such that final values are provided for the respective variables for each patient;
    the mining resulting in a separate factoid for each variable of the plurality of variables, the separate factoids for the plurality of variables being provided by the mining for each of the patients from the different data sources;
    compiling, with the processor, the factoids into a plurality of structured patient records of a structured computerized patient record database and associated with patient variables for each of the patients, each structured patient record for respective patients comprising the factoids; and
    correlating, with a system, an outcome with the factoids associated with patient variables;
    wherein correlating comprises correlating the outcome from the factoids.

2. The method as in claim 1, further comprising:
    inputting at least one patient criteria relating to the disease of interest; and
    extracting at least one structured patient record matching the at least one patient criteria; and
    determining the outcome of the at least one structured patient record.

3. The method as in claim 2, further comprising the steps of changing a value of the at least one patient criteria and repeating the extracting and determining steps.

4. The method as in claim 1, wherein the plurality of first patient records are stored in structured and unstructured sources, the data mining converting unstructured information into structured information.

5. The method as in claim 1, wherein the plurality of first patient records are collected over a course of treatment of a plurality of patients.

6. The method as in claim 2, further comprising correlating a plurality of criteria to a plurality of patient outcomes.

7. The method as in claim 6, further comprising suggesting a hypothesis for a clinical trial based on the correlation.

8. The method as in claim 7, further comprising validating the hypothesis by performing a retrospective study on the plurality of structured patient records.

9. A system for analyzing a plurality of patient records, the plurality of patient records being stored in structured and unstructured sources, the system comprising:
    a data miner for mining information from the plurality of first patient records including the unstructured sources using a domain knowledge base relating to a disease of interest, the data miner configured to:
    mine from a plurality of different data sources including the unstructured sources for each of the first patient records, each of the first patient records being for a respective patient;
    for each of a plurality of variables for each patient, extract different values from multiple of the different data sources such that multiple of the values are provided for each of the variables representing the patient at a same time;
    for each of the plurality of variables for each patient, assign a probabilistic assertion to each of the values from the different data sources such that the multiple values for each variable are each assigned a probability resulting in different values and respective probabilistic assertions for each variable of the plurality of variables representing each patient; and
    for each of the plurality of variables for each patient, combine by inference the probabilities for each of the values from the different data sources into a unified probability for the respective variable, the unified probability providing a factoid representing a final value for the respective variable such that final values are provided for the respective variables for each patient;
    the mining resulting in a separate factoid for each variable of the plurality of variables, the separate factoids for the plurality of variables being provided by the mining for each of the patients from the different data sources;
    the data miner compiling mined data as the factoids, the mined data being from the unstructured sources, into a plurality of structured patient records of a structured computerized patient record database and associated with patient variables for each of the patients, each structured patient record for respective patients comprising the factoids;
    a processor operable to correlate an outcome with the mined data associated with the patient variables as a function of at least one of the structured patient records;
    wherein the processor is operable to correlate the outcome from the factoids.

10. The system as in claim 9, further comprising an interface for inputting at least one patient criteria relating to the disease of interest, wherein the processor is operable to extract the at least one of the structured patient records as a function of the patient criteria.

11. The system as in claim 10, wherein the processor is operable to correlate a plurality of criteria to a plurality of patient outcomes.

12. The system as in claim 11, wherein the processor is operable to suggest a hypothesis for a clinical trial based on the correlation.

13. The method of claim 1, wherein compiling the mined data into a plurality of structured patient records associated with patient variables comprises compiling into structured patient records associated with patient states, treatment, or combinations thereof.

14. The system of claim 9, wherein the processor is operable to correlate the outcome with patient states, treatment, or combinations thereof.

15. The method of claim 1 wherein data mining comprises data mining free text using the domain knowledge base, the data mining identifying values of variables related to the disease of interest.

16. The method of claim 2 further comprising:
   outputting an illustration of the outcome as a function of different values of a first of the possible patient variables.

17. The method of claim 1 further comprising:
   determining patient records matching a guideline from a prospective clinical trail; and
   performing the compiling and correlating with the patient records matching the guideline but restricted to a category of patients not included in the prospective clinical trail.

* * * * *